(12) United States Patent
Gagnon et al.

(10) Patent No.: US 6,171,243 B1
(45) Date of Patent: Jan. 9, 2001

(54) COMBINATION OF COLLIMATED AND COINCIDENCE INFORMATION FOR POSITRON IMAGING

(75) Inventors: Daniel Gagnon; Frank P. DiFilippo, both of Mayfield Heights, OH (US)

(73) Assignee: Picker International, Inc., Cleveland, OH (US)

(*) Notice: Under 35 U.S.C. 154(b), the term of this patent shall be extended for 0 days.

(21) Appl. No.: 08/865,923

(22) Filed: May 30, 1997

(51) Int. Cl.[7] ........................................... A61B 5/00
(52) U.S. Cl. ............... 600/431; 250/363.04; 250/363.03; 600/425
(58) Field of Search ......................... 250/363.04, 363.03, 250/365, 369; 600/431, 425, 407

(56) References Cited

U.S. PATENT DOCUMENTS

| | | | |
|---|---|---|---|
| 5,210,421 | * 5/1993 | Gullberg et al. | 250/363.04 |
| 5,283,813 | * 2/1994 | Shalvi et al. | 375/12 |
| 5,421,330 | * 6/1995 | Thirion et al. | 128/653.1 |
| 5,462,056 | * 10/1995 | Hawman et al. | 128/659 |
| 5,519,222 | * 5/1996 | Besett | 250/363.04 |
| 5,532,490 | * 7/1996 | Gullberg et al. | 250/363.04 |
| 5,565,684 | * 10/1996 | Gullberg et al. | 250/363.04 |
| 5,585,637 | * 12/1996 | Bertelsen et al. | 250/363.03 |
| 5,672,877 | * 9/1997 | Liebig et al. | 250/363.04 |

* cited by examiner

Primary Examiner—William E. Kamm
Assistant Examiner—Eleni Mantis Mercader
(74) Attorney, Agent, or Firm—Timothy B. Gurin; John J. Fry

(57) ABSTRACT

A diagnostic imaging system includes oppositely disposed radiation detectors (32, 34) configured to detect coincidence radiation events caused by a substance injected into a subject which generates positron emissions. A coincidence data processor (40) collects and processes the radiation detected by the detectors (32, 34) and a coincidence circuitry (44) matches and compares the detected events to determine coincidence. Coincidence data is generated and stored in a coincidence data memory (46). A collimated radiation detector (50) is disposed at an angle to the coincidence radiation detectors (32, 34) and is configured to detect single photon radiation traveling along a selected projection path determined by a collimator (52) mounted on a front face of the collimated radiation detector (50). A single photon data processor (60) generates collimated data (74) based on the radiation detected by the collimated radiation detector (50). A combiner (80) selectively combines the coincidence data (46) and the collimated data (74) and the combined data is reconstructed into an image representation (84) of a region of interest.

12 Claims, 7 Drawing Sheets

COMBINATION OF COLLIMATED AND COINCIDENCE INFORMATION FOR POSITRON IMAGING

BACKGROUND OF THE INVENTION

The present invention relates to the art of diagnostic imaging. It finds particular application in conjunction with nuclear or gamma cameras and will be described with particular reference thereto. It is to be appreciated, however, that the present invention will also find application in other non-invasive investigation techniques and imaging systems such as single photon planar imaging, whole body nuclear scans, positron emission tomography (PET) and other diagnostic modes.

Positron emission tomography (PET) scanners are known as coincidence imaging devices. In planar coincidence imaging, two radiation detectors oppose each other with a subject disposed between the detectors. Typically, one or more radiopharmaceuticals or radioisotopes capable of generating positron emission radiation are injected into the subject. The radioisotope preferably travels to an organ of interest whose image is to be produced. The detectors scan the subject along a longitudinal axis without rotation producing a data set with incomplete angular sampling, otherwise known as limited angle tomography. Radiation events are detected on each detector and a coincidence circuitry compares and temporally matches the events on each detector. Events on one detector which have a coincident event on the other detector are treated as valid data and may be used in image reconstruction.

Typically, the detector includes a scintillation crystal that is viewed by an array of photomultiplier tubes. The relative outputs of the photomultiplier tubes are processed and corrected, as is conventional in the art, to generate an output signal indicative of (1) a position coordinate on the detector head at which each radiation event is received, and (2) an energy of each event. The energy is used to differentiate between various types of radiation such as multiple emission radiation sources and to eliminate noise, or stray and secondary emission radiation. A two-dimensional image representation is defined by the number of coincidence radiation events or counts received at each coordinate. However during a scan, only a fraction of the events detected are coincidence events. As such, scan times are increased in an effort to obtain a sufficient data sampling for image reconstruction which poses additional inconveniences to the subject and an increase in scanning costs from reduced patient throughput.

The present invention provides a new and improved diagnostic imaging system and method which provides diagnostic information in addition to coincidence events which overcomes the above-referenced problems and others.

SUMMARY OF THE INVENTION

In accordance with the present invention, a new and improved diagnostic imaging system and method for diagnostic imaging is provided. The diagnostic imaging system includes a gantry which defines an examination region that receives a subject where the subject includes a positron emitter and a single photon emitter. First and second radiation detectors are oppositely disposed on the gantry and have the examination region therebetween. The first and second radiation detectors detect radiation from the examination region. A coincidence circuit is connected to the first and second radiation detectors and determines coincidence radiation events emitted from the positron emitter. Coincidence data is generated based on the coincidence radiation events. A third radiation detector which includes a collimator, detects collimated radiation traveling along a selected projection path. The third radiation detector is supported on the gantry at an angle to the first and second radiation detectors. A projection data processor is connected to the third radiation detector and generates collimated projection data based on collimated radiation detected from the single photon emitter. A combiner selectively combines the coincidence data and the collimated projection data into an image volume and a reconstruction processor reconstructs an image representation from the image volume.

In a more limited aspect of the present invention, the diagnostic imaging system further includes a transmission radiation source which generates transmission radiation toward the examination region. The third radiation detector detects both the transmission radiation from the transmission radiation source and emission radiation from the subject. A sorter sorts the emission and transmission radiation detected. The projection data processor generates transmission projection data based on the transmission radiation detected and selectively combines the transmission projection data with the collimated projection data.

In accordance with another aspect of the present invention, a diagnostic imaging system is provided including a gantry which supports a plurality of radiation detectors which detect coincidence radiation emitted from a subject disposed in an examination region. A processor generates coincidence data from the detected coincidence radiation and a reconstruction processor reconstructs the coincidence data into an image representation of a selected portion of the subject. The diagnostic imaging system further includes a collimated radiation detector which detects collimated radiation from the examination region. A collimation data processor generates collimated radiation data based on the collimated radiation detected and the collimated radiation data is selectively combined with the coincidence data before reconstruction by the reconstruction processor.

One advantage of the present invention is that a positron imaging system which generates coincidence events is combined with a single photon imaging system.

Another advantage of the present invention is that image reconstruction is improved by combining coincidence data with collimated data.

Yet another advantage is that sufficient image quality may be obtained in a shorter scan time, thereby improving patient throughput and minimizing patient inconvenience. Still another advantage is that the production of whole body planar images with additional depth information, PET images with transmission attenuation, and combined PET/SPECT, dual isotope imaging is facilitated.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
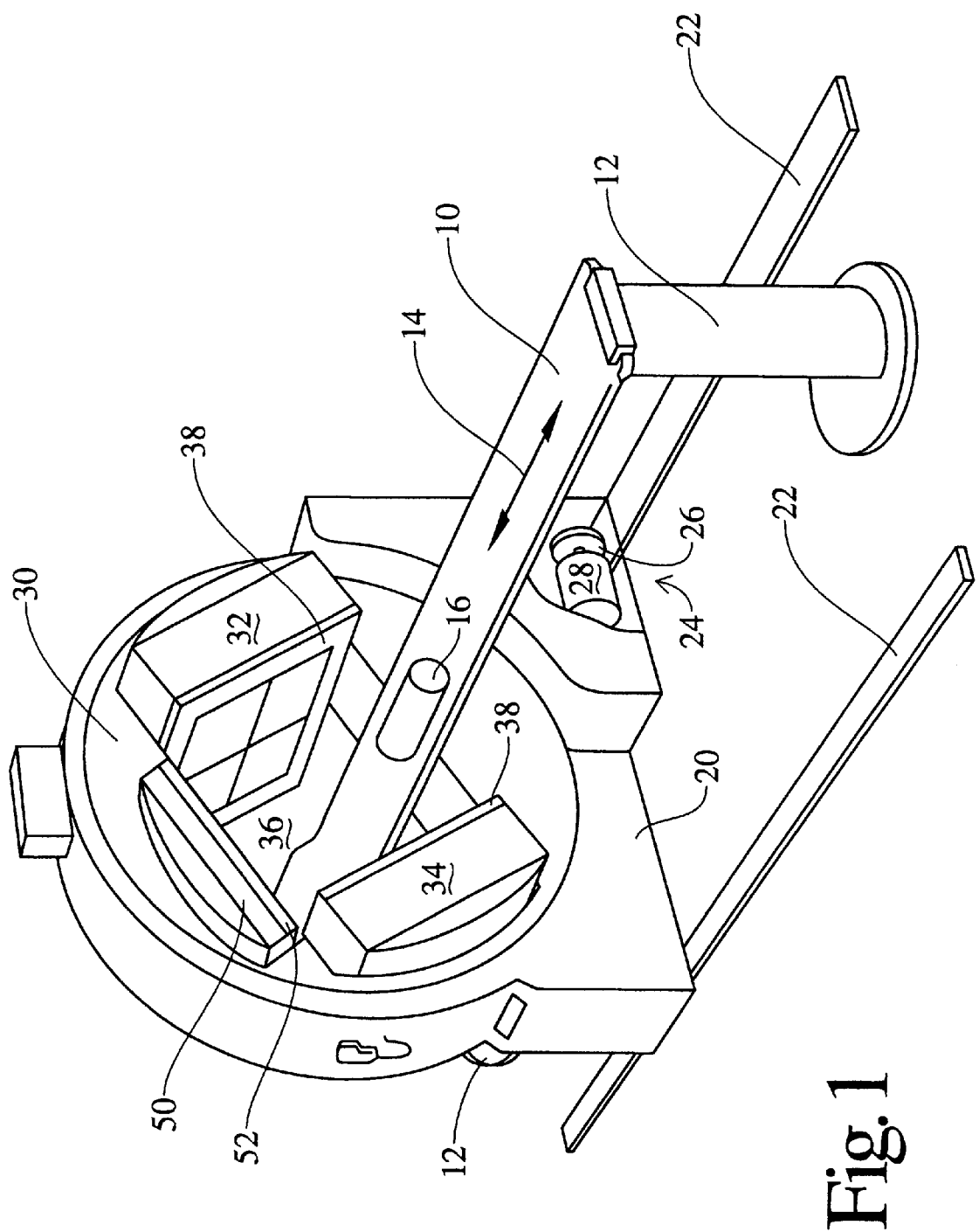
FIG. 1 is a diagrammatic illustration of a diagnostic imaging system in accordance with the present invention.

With reference to FIG. 1, a diagnostic imaging system includes a subject support or table 10 which is mounted to stationary, vertical supports 12 at opposite ends. The subject table is selectively positionable up and down to center a subject 16 in the center of a circle along a longitudinal axis 14.

An outer gantry structure 20 is movably mounted on tracks 22 which extend parallel to the longitudinal axis. This enables the outer gantry structure to be moved parallel to the longitudinal axis 14. An outer gantry structure moving assembly 24 is provided for selectively moving the outer gantry structure 20 along the tracks 22 in a path parallel to the longitudinal axis. In the illustrated embodiment, the longitudinal moving assembly includes drive wheels 26 for supporting the outer gantry structure on the tracks. A motive power source, such as a motor 28, selectively drives one of the wheels which frictionally engages the track and drives the outer gantry structure and supported inner gantry structure and detector heads therealong. Alternately, the outer gantry can be stationary and the subject support configured to move the subject along the longitudinal axis.

An inner gantry structure 30 is rotatably mounted on the outer gantry structure 20. A first camera or radiation detector head 32 is mounted to the inner gantry structure. A second radiation detector head 34 is mounted to the inner gantry structure opposite to the first camera head. The first and second detectors 32, 34 are configured to detect positron annihilation radiation generated by a positron emission source injected into the subject. The inner gantry structure defines a central, subject receiving examination region 36 for receiving the subject table and, particularly along the longitudinal axis. The examination region 36 is enlarged to receive the detector heads in any of a variety of displacements from a central axis and angular orientations.

The detectors each include a scintillation crystal disposed behind a radiation receiving face 38 that is viewed by an array of photomultiplier tubes. The scintillation crystal emits a flash of light in response to incident radiation. The array of photomultiplier tubes convert the light into electrical signals. A resolver circuit resolves the x,y-coordinates of each light flash and the energy of the incident radiation. The relative outputs of the photomultiplier tubes are processed and corrected, as is conventional in the art, to generate an output signal indicative of a position coordinate on the detector head at which each radiation event is received, and an energy of each event.

A coincidence data processor or coincidence imaging subsystem 40 collects 42 the position coordinates and energy values obtained based on the radiation events detected by each detector 32 and 34. A coincidence circuitry 44 compares and matches radiation events from positron emissions 58 generated by a positron emitter within the subject and were coincidentally detected by the detectors 32 and 34. Based on the coincidence events, the coincidence data processor generates coincidence data which is stored in a coincidence memory 46.

The diagnostic imaging system includes a third radiation detector head 50 supported by the gantry which is disposed at an angle to the coincidence radiation detectors 32, 34. The third detector is configured to acquire projection radiation data and includes a collimator 52 mounted on a front face to restrict received radiation to radiation traveling generally perpendicular to the face. Of course, various types of collimators can be used to obtain a desired projection path such as a parallel beam, a cone beam or fan beam geometry. The third detector 50 includes a scintillation crystal that is viewed by an array of photomultiplier tubes. The relative outputs of the photomultiplier tubes are processed and corrected to generate an output signal indicative of a position coordinate on the detector at which each radiation event is received, and an energy of each event.

Figure 2:
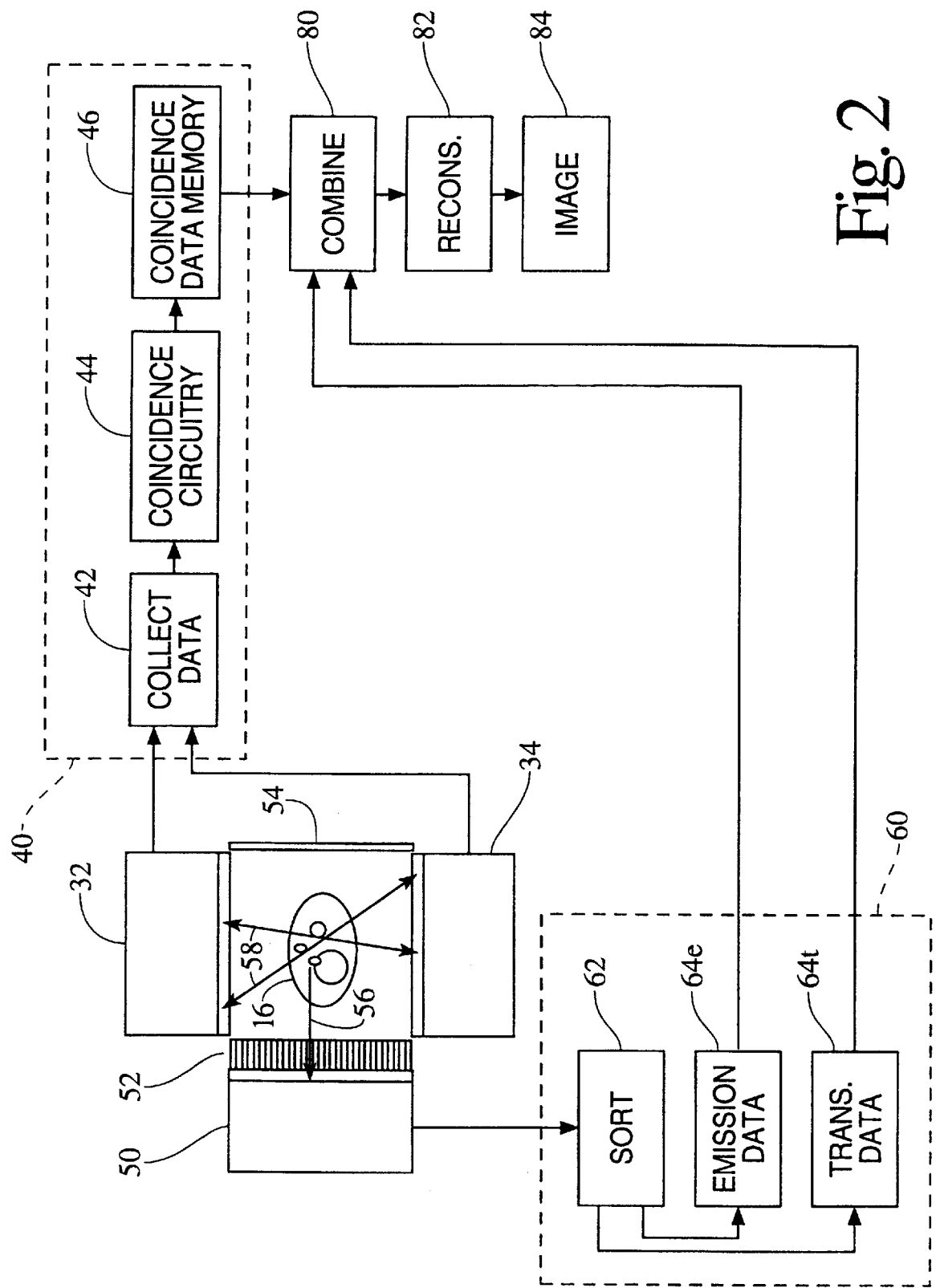
FIG. 2 is an illustration of one embodiment of a coincidence radiation detector system and a collimated radiation detector system in accordance with the present invention.

With reference to FIG. 2, the diagnostic imaging system includes a transmission radiation source 54 disposed across from the third radiation detector with the examination region 36 disposed therebetween. The transmission radiation source transmits radiation having a different energy level than the injected radioisotopes throughout the examination region which is detected by the third radiation detector. However, the transmission radiation may have the same energy level as the emission radiation in which case the radiation is differentiated by the positions on the detector. In the preferred embodiment, the collimator is a high energy collimator capable of handling 511 keV gamma radiation and limits the radiation received by the third radiation detector to be projections normal to the coincidence geometry. With the transmission radiation source, the third radiation detector receives both transmission and emission radiation.

With further reference to FIG. 2, an exemplary single photon data processor 60 is provided for the collimated third detector 50. Both 511 keV positron annihilation radiation emitted from the subject and transmission radiation from the transmission radiation source 54 is received by the third detector 50. A sorter 62 sorts the emission projection data and the transmission projection data based on the energy of the detected radiation. The data may also be sorted based solely on the location of the detected event, or based on a combination of energy and location. The sorted data are stored in a projection view memory 64, more specifically in corresponding emission data memory 64e and transmission data memory 64t.

The collimated projection data 64e, 64t obtained is particularly useful in rapid whole-body limited angle tomography. The collimated data 64e, 64t is optimally obtained simultaneously with the coincidence events. Thus, the diagnostic imaging system is capable of operating a variety of detectors in different modes. A combiner 80 combines the information from the collimated data 64e, 64t with the coincidence data 46 in several different ways in order to supplement the coincidence data 46. In one embodiment, the collimated data 64e, 64t is used to define a boundary outline of a region of interest within the subject so as to limit the range of reconstruction required for a limited angle tomography. Alternately, the collimated data 64e, 64t is used to establish the number of counts per plane which is used to further constraint the reconstruction of the coincidence data 46 so that information unrelated to the region of interest is not reconstructed. In another alternative, the collimated information 64e, 64t is reconstructed together with the coincidence data 46. A reconstruction processor 82 reconstructs the combined coincidence and collimated data into an image representation 84, for example, by a blind deconvolution-type technique which reconstructs different types of data. An example of a blind deconvolution technique is discussed in "Blind Image Deconvolution," by Kundur and Hatzinkos, IEEE Signal Processing Magazine, Vol.13, No. 3, page 43, 1996.

Figure 3:
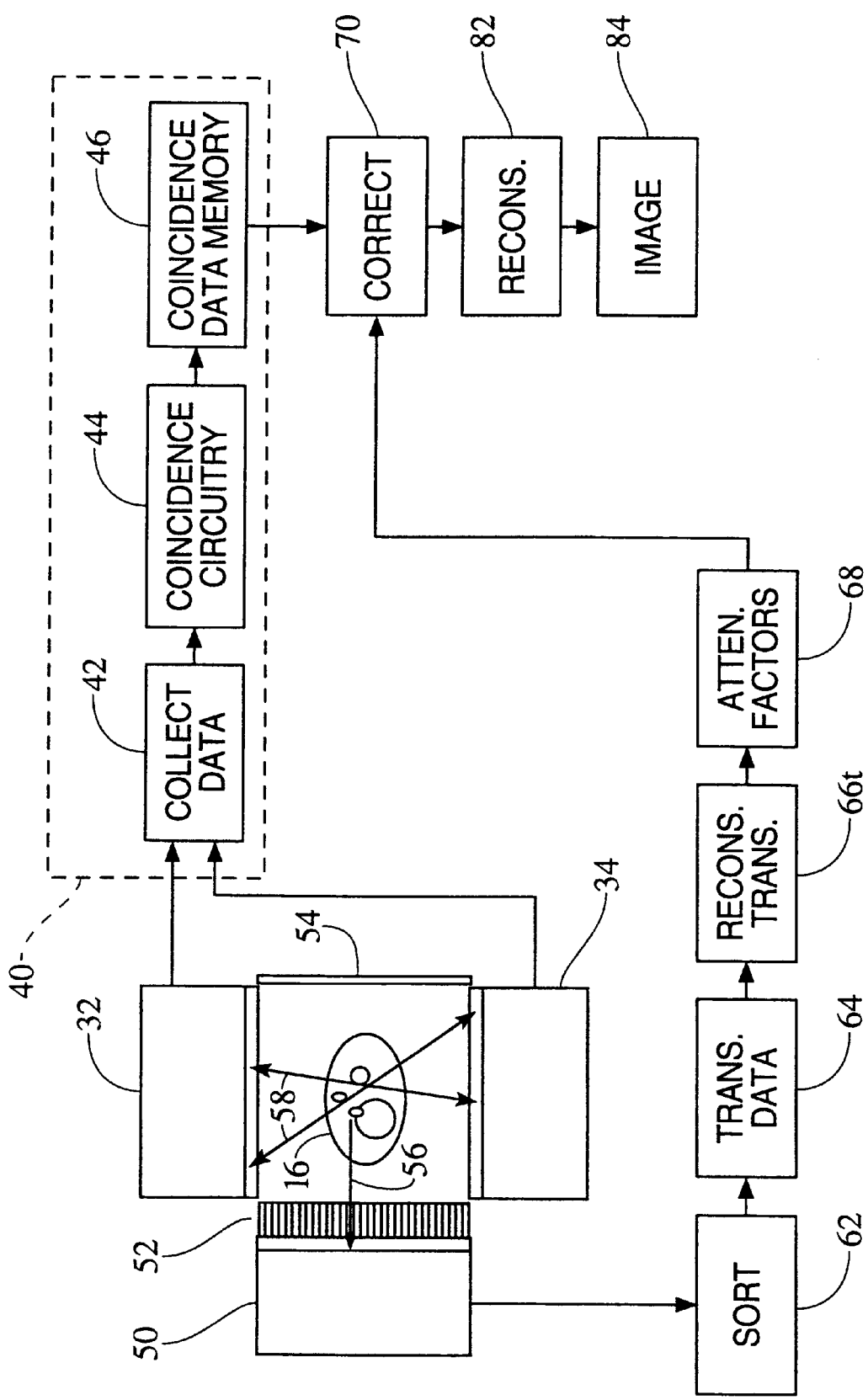
FIG. 3 is an example of an alternative embodiment of the present invention.

With reference to FIG. 3, the diagnostic imaging system may also be used to produce transmission attenuation corrected PET images. As the gantry and hence the detectors 32, 34, 50 are rotated about the patient, data received by the detectors 32, 34 is collected 42 and processed by the coincidence circuitry 40 as described above. Valid coincidence events are stored in a coincidence projection view memory 46. Simultaneously, transmission radiation from the transmission radiation source 54 is received by the third detector 50. A sorter 62 selects the transmission data based on energy of detected radiation, discarding detected events which do not correspond in energy to that of the transmission radiation source 54. Alternately, the data may be sorted based on the position of the detected event, either alone or in combination with its energy. The data are stored in a transmission projection view memory 64.

The coincidence data normally contains inaccuracies caused by varying absorption characteristics of the patient's anatomy. A reconstruction processor 66t reconstructs the transmission data into a transmission image representation of volume attenuation factors stored in a memory 68. Each voxel value is indicative of attenuation of tissue in a corresponding location within the patient. A coincidence data correction means 70 corrects the coincidence data in accordance with the attenuation factors determined from the transmission data. More specifically, for each ray along which coincidence data is received, the correction means calculates a corresponding ray through the transmission attenuation factors. Each ray of the coincidence data is then weighted or corrected 70 in accordance with the attenuation factors and reconstructed by a coincidence radiation reconstruction processor 82 to generate a three-dimensional coincidence image representation 84 of the patient.

Figure 4:
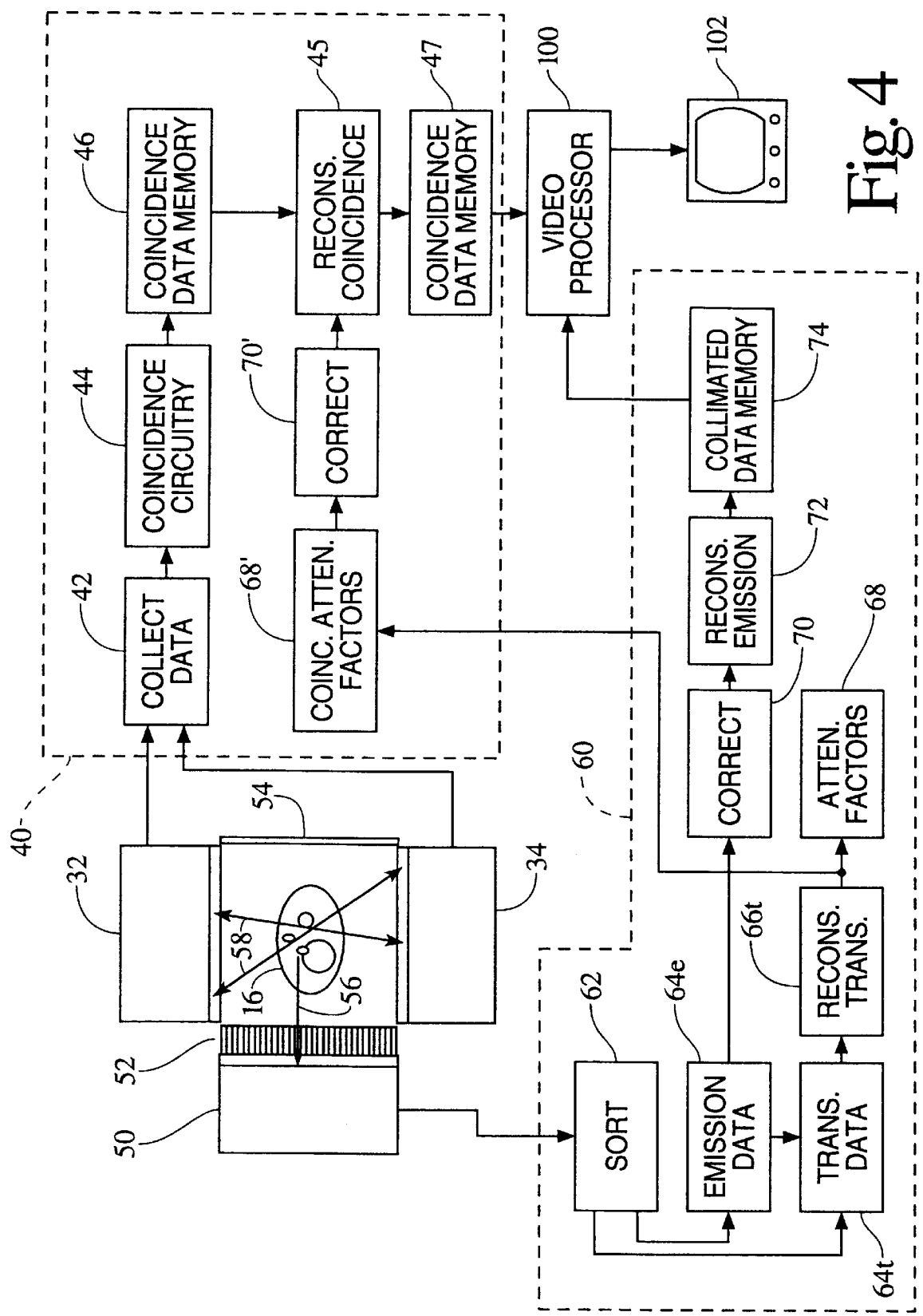
FIG. 4 is an example of a diagnostic system to simultaneously collect data from coincidence PET and SPECT images in accordance with the present invention.

With reference to FIG. 4, the diagnostic imaging system may also be used to simultaneously collect data for coincidence PET and SPECT images in dual isotope imaging. For example, a radiopharmaceutical which produces positron radiation (e.g., 18 F-FDG) and a radiopharmaceutical which produces single photon emission radiation (e.g., $^{99m}$Tc-MIBI) may both be introduced into the subject.

As the gantry and hence the detectors 32, 34, 50 are rotated about the patient, data received by the detectors 32, 34 is collected 42 and processed by the coincidence circuitry 44. Valid coincidence events are stored in a coincidence projection view memory 46. Simultaneously, single photon emission data from the subject and transmission radiation from the transmission radiation source 54 are received by the third detector 50. A sorter 62 sorts the emission projection data and the transmission projection data on the basis of relative energies. Alternately, the data may be sorted based on the position of the detected event either alone or in combination with the energy of the event. The data are stored in a projection view memory 64, more specifically in emission data memory 64e and transmission data memory 64t.

The emission data normally contains inaccuracies caused by varying absorption characteristics of the patient's anatomy. A reconstruction processor 66t reconstructs the transmission data into a transmission image representation of volume attenuation factors stored in a memory 68. Each voxel value is indicative of attenuation of tissue in a corresponding location within the patient. An emission data correction means 70 corrects the emission data in accordance with the emission data attenuation factors 68 determined from the transmission data. More specifically, for each ray along which emission data is received, the emission correction means calculates a corresponding ray through the transmission attenuation factors. Each ray of the emission data is then weighted or corrected 70 in accordance with the attenuation factors and reconstructed by an emission radiation reconstruction processor 72 to generate a three-dimensional emission image representation that is stored in a collimated data memory 74. Alternately, the corrected emission data is directly stored in the collimated data memory 74 without reconstruction.

The coincidence data may also contain inaccuracies caused by varying absorption characteristics of the patient's anatomy. Accordingly, a coincidence data correction means 70' corrects the coincidence data in accordance with coincidence data attenuation factors 68'. FIG. 4 depicts the coincidence attenuation factors as being different from those for the emission data 68, reflecting the different energy of the respective radiation. Alternately, the same correction factors may be used. A coincidence reconstruction processor 45 reconstructs the coincidence data to generate a three-dimensional coincidence image representation that is stored in a coincidence data memory 47. Selected portions of the coincidence image 47 and the emission image 74 may then be processed by video processor 100 and displayed on video monitor 102 or in other suitable human readable form. Hence, a single diagnostic imaging system may be used to simultaneously generate attenuation corrected coincidence PET and attenuation corrected SPECT images.

In the event that attenuation correction of the emission data, the coincidence data, or both is not required, the associated attenuation correction processing may be deleted.

Figure 6:
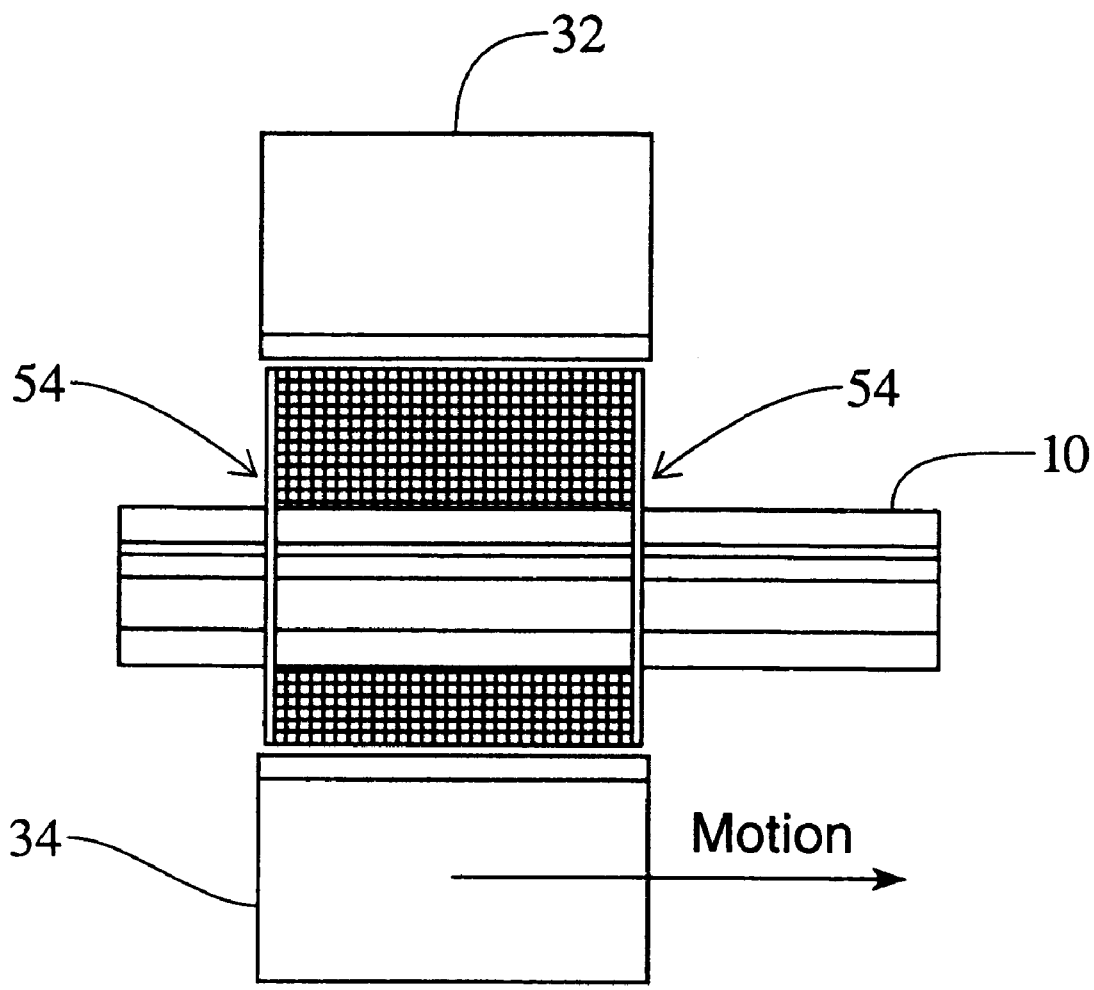
FIG. 6 is an illustration of another alternative embodiment which includes one or more transmission radiation sources.

In yet another alternative embodiment and with reference to FIG. 6, one or more fixed collimated transmission radiation sources 54 are disposed on the gantry. Radiation detection areas of the collimated radiation detector 50 only in front of the radiation sources 54 are used to acquire the transmission data while the remaining areas of the collimated radiation detector 50 are used to acquire only emission radiation while the first and second radiation detectors 32, 34 continue to operate in detecting coincidence events. In this way, transmission data may be collected for various portions of the anatomy as the gantry and patient are moved relative to each other. Thus, a drive mechanism for scanning or sweeping the transmission source or sources 54 across the face of the third detector 50 is not required.

Alternatively, a transmission radiation line source 54 may be moveably mounted to one of the detectors 32, 34 such that the line source 54 may be scanned or swept across the face of the detector 50. The collimated radiation detector 50 acquires both transmission and emission data in coordination with the movement of the line source 54.

Figure 7:
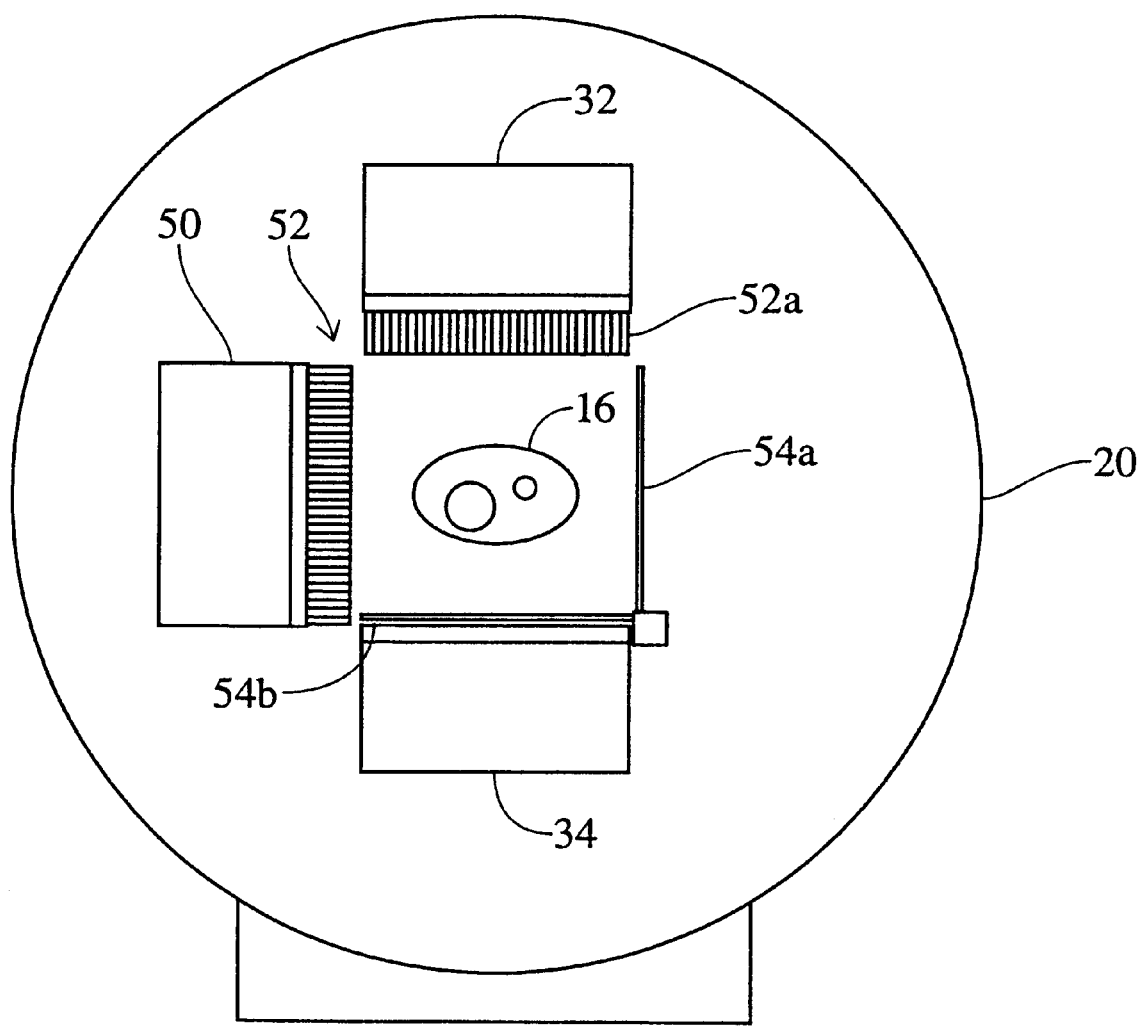
FIG. 7 illustrates a line source configuration in accordance with the present invention.

A line source configuration which is particularly advantageous in connection with cardiac SPECT imaging is shown in FIG. 7. In this configuration, the detector 50 is fitted with a collimator 52 and the detector 32 is fitted with a collimator 52a. Data from both detectors is collected as traditional single photon data. Two transmission radiation sources 54a, 54b are moveably mounted to the detector 34 such that the transmission sources 54a, 54b may be scanned or swept across the face of the detectors 50 and 32, respectively. The transmission source 54a is generally parallel to the face of the detector 50, while the transmission source 54b is perpendicular to the transmission source 54a and generally parallel to the face of the detector 32. Such an arrangement facilitates efficient generation of attenuation corrected cardiac SPECT data. Preferably, the line source 54a and the collimator 52a are each mounted so as to be readily installed in and removed from their respective mounting positions. With the line source 54a and the collimator 52a removed, the imaging device can be readily converted to collect coincidence and collimated data as described above.

Those skilled in the art will recognize that exemplary reconstruction technique for emission and transmission data have been described. Of course, the reconstruction technique varies according to the type and energy of the radiation collected and type of collimator used (i.e., fan, cone, parallel beam). Even using the same type and energy and collimator type, there are various possible reconstruction techniques, producing different image qualities at different execution speeds, as is well-known in the art.

Figure 5:
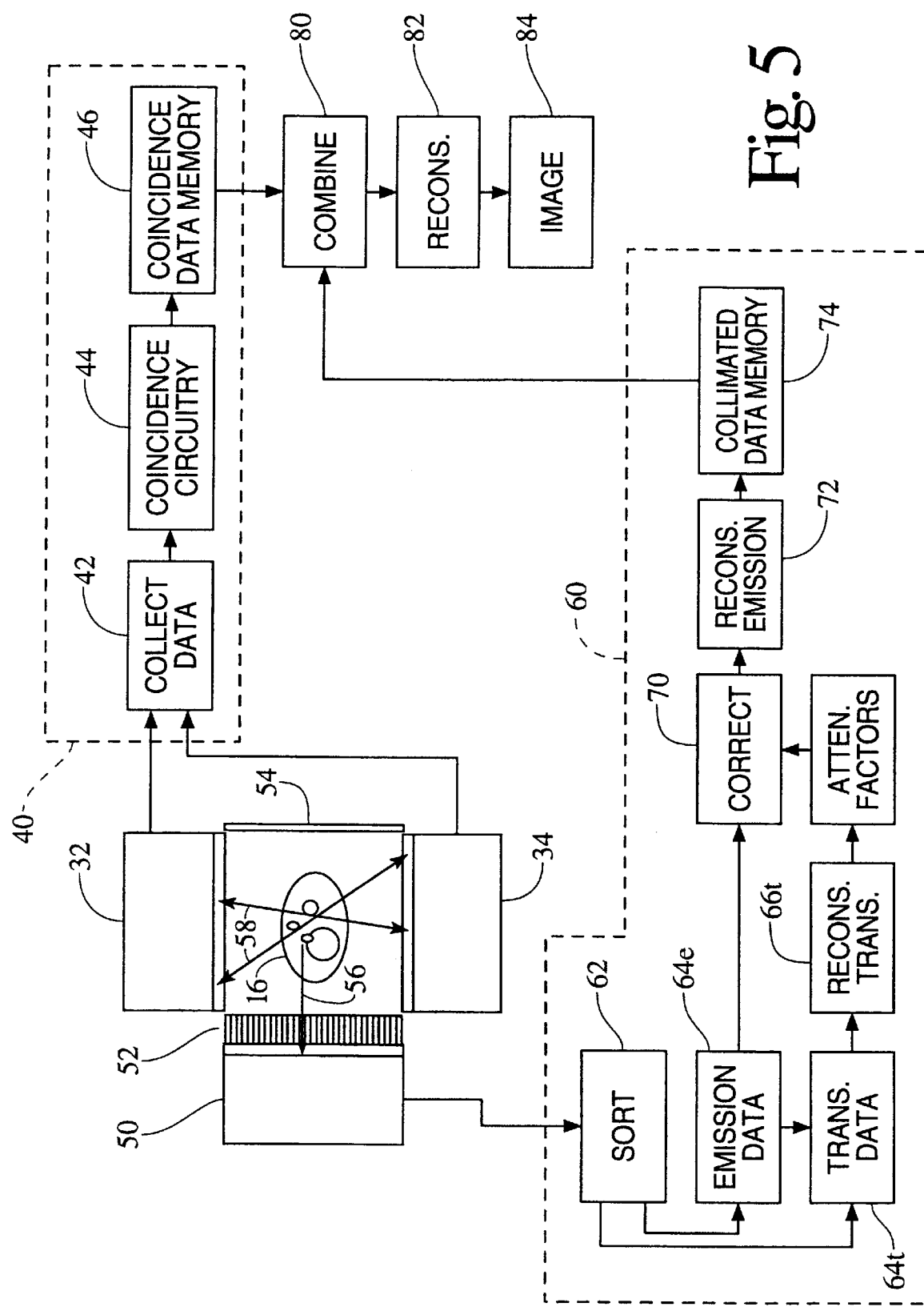
FIG. 5 is an example of another alternative embodiment of the present invention.

With reference to FIG. 5, an exemplary single photon data processor or single photon imaging subsystem 60 is provided for the collimated third detector 50 which detects single photon radiation 56. Furthermore, an exemplary reconstruction technique for emission and transmission data is provided. Of course, the reconstruction technique changes according to the types of radiation collected and the types of collimators used (i.e., fan, cone, parallel beam). Both emission radiation from the subject and transmission radiation from the transmission radiation source 54 is received by the third detector 50 and emission projection data is generated. The emission data normally contains inaccuracies caused by varying absorption characteristics of the subject's anatomy. A sorter 62 sorts the emission projection data and transmission projection data on the basis of the relative energies. The data are stored in a projection view memory 64, more specifically in corresponding emission data memory 64e and transmission data memory 64t. A reconstruction processor 66t reconstructs the transmission data into a transmission image representation or volume of attenuation factors stored in a memory 68. Each voxel value stored in the memory 68 is indicative of attenuation of tissue in a corresponding location within the patient. An emission data correction means 70 corrects the emission data in accordance with the attenuation factors determined from the transmission data. More specifically, for each ray along which emission data is received, the emission correction means calculates a corresponding ray through the transmission attenuation factors stored in the memory 68. Each ray of the emission data is then weighted or corrected 70 in accordance with the attenuation factors and reconstructed by an emission radiation reconstruction processor 62 to generate a three-dimensional emission image representation that is stored in a collimated data memory 74. Alternately, the corrected emission data is directly stored in the collimated data memory without reconstruction.

The collimated projection data 74 obtained is particularly useful in rapid whole-body limited angle tomography. The collimated data 74 is optimally obtained simultaneously with the coincidence events. Thus, the diagnostic imaging system is capable of operating a variety of detectors in different modes. A combiner 80 combines the information from the collimated data 74 with the coincidence data 46 in several different ways in order to supplement the coincidence data 46. In one embodiment, the collimated data 74 is used to define a boundary outline of a region of interest within the subject so as to limit the range of reconstruction required for a limited angle tomography. Alternately, the collimated data 74 is used to establish the number of counts per plane which is used to further constraint the reconstruction of the coincidence data 46 so that information unrelated to the region of interest is not reconstructed. In another alternative, the collimated information 74 is reconstructed together with the coincidence data 46. A reconstruction processor 82 reconstructs the combined coincidence and collimated data into an image representation 84, for example, by a blind deconvolution-type technique which reconstructs different types of data. An example of a blind deconvolution technique is discussed in "Blind Image Deconvolution," by Kundur and Hatzinkos, IEEE Signal Processing Magazine, Vol. 13, No. 3, page 43, 1996.

Those skilled in the art will recognize that the present invention facilitates the combination of coincidence and single photon projection data. In particular, the detector and source configuration described above is particularly useful for producing whole body planar coincidence images with additional depth information, PET images with transmission attenuation correction, and combined PET/SPECT dual isotope imaging, either with or without transmission attenuation correction.

With the use of a stationary source and by moving the detector during a scan, attenuation information is obtained. Alternately, two or more stationary sources are disposed at each end of the third detector and the third detector is moved during a scan. This decreases "ramp-up" distance for the attenuation information when part of the patient is in the field of view when scan starts and/or ends.

A video processor withdraws selected portions of the data from the reconstructed image to generate corresponding human-readable displays on a video monitor. Typical displays include reprojections, selected slices or planes, surface renderings, whole-body tomographic images and the like.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A nuclear camera system comprising:
   a gantry defining an examination region for receiving a subject, the subject including one of (i) a positron emitter and (ii) a positron emitter and a single photon emitter;
   first and second radiation detectors oppositely disposed on the gantry and having the examination region therebetween, the first and second radiation detectors detecting radiation from the examination region;
   a coincidence circuit connected to the first and second radiation detectors for determining coincidence radiation events emitted from the positron emitter and generating coincidence data based on the coincidence radiation events;
   a third radiation detector including a collimator for detecting, concurrently with the detection of radiation by the first and second radiation detectors, collimated radiation traveling along a selected projection path, the third radiation detector being supported on the gantry at an angle to the first and second radiation detectors;

a projection data processor connected to the third radiation detector for generating collimated projection data based on collimated radiation detected by the third radiation detector;

a combiner which selectively combines the coincidence data and the collimated projection data into an image volume; and a reconstruction processor for reconstructing an image representation from the image volume.

2. The nuclear camera system as set forth in claim 1 further including:

a transmission radiation source for generating transmission radiation toward the examination region, the third radiation detector detecting both the transmission radiation from the transmission radiation source and emission radiation from the subject;

a sorter connected to the third radiation detector for sorting the emission radiation and the transmission radiation detected; and the projection data processor generating transmission projection data based on the transmission radiation detected and selectively combining the transmission projection data with the collimated projection data.

3. The nuclear camera system as set forth in claim 1 further including:

a motor assembly for selectively moving the gantry along a non-rotating path along a longitudinal axis.

4. The nuclear camera system as set forth in claim 3 wherein the motor assembly selectively rotates the gantry around the examination region.

5. A diagnostic system including a gantry supporting a plurality of radiation detectors for detecting coincidence radiation emitted from a subject disposed in an examination region, a processor for generating coincidence data from the detected coincidence radiation, and a reconstruction processor for reconstructing the coincidence data into an image representation of a selected portion of the subject, the diagnostic imaging system comprising:

a collimated radiation detector for detecting, concurrently with the detection of radiation by the plurality of radiation detectors for detecting coincidence radiation, collimated radiation from the examination region; and a collimation data processor for generating collimated radiation data based on the collimated radiation detected, the collimated radiation data being selectively combined with the coincidence data before reconstruction by the reconstruction processor.

6. The diagnostic imaging system as set forth in claim 5 further including:

a transmission radiation source for generating transmission radiation towards the examination region, the collimated radiation detector detecting both transmission radiation and emission radiation;

a sorter for sorting the transmission radiation and emission radiation detected, the collimation data processor generating transmission radiation data based on the transmission radiation detected and generating emission radiation data based on the emission radiation detected; and a combiner for selectively combing the transmission and emission data to form the collimated radiation data.

7. The diagnostic imaging system as set forth in claim 5 wherein the processor includes coincidence circuitry for determining coincidence events from radiation detected by the plurality of radiation detectors.

8. The diagnostic imaging system as set forth in claim 5 further including a combiner which selectively combines the collimated radiation data and the coincidence data.

9. The diagnostic imaging system as set forth in claim 5 further including:

means for detecting positron emission radiation emitted from the subject being diagnosed and generating positron emission data in accordance with the detected positron emission radiation;

means for detecting single photon emission radiation emitted from the subject and generating single photon emission data in accordance with the detected single photon emission radiation; and means for reconstructing an image representation of a region of interest of the subject based on a combination of the positron emission data and the single photon emission data.

10. A method of diagnostic imaging with a nuclear camera system including an examination region having a subject disposed therein, the method comprising:

injecting the subject with first and second isotopes, the first isotope generating positron emission radiation and the second isotope generating single photon emission radiation;

detecting coincidence radiation events from the positron emission radiation;

generating coincidence data based on the coincidence radiation events detected;

concurrently with the step of detecting coincidence radiation events, detecting single photon emissions from the single photon emission radiation;

generating single photon emission data based on the single photon emissions detected;

combining the coincidence data and the single photon emission data into an image volume; and reconstructing an image representation of the subject from the image volume.

11. The method of diagnostic imaging as set forth in claim 10 further including:

transmitting transmission radiation through the examination region;

detecting the transmission radiation and generating transmission data based on the transmission radiation detected; and combining the transmission data, the single photon emission data and the coincidence data into the image volume.

12. The method of diagnostic imaging as set forth in claim 10 wherein the reconstructing includes blind deconvolution.

* * * * *